US005925014A

United States Patent [19]

Teeple Jr.

[11] Patent Number: 5,925,014

[45] **Date of Patent: *Jul. 20, 1999**

[54] METHOD AND APPARATUS FOR PREPARING AND ADMINISTERING INTRAVENOUS ANESTHESIA INFUSIONS

[76] Inventor: Edward Teeple Jr., 40 St. Clair Dr., Pittsburgh, Pa. 15228

[ * ] Notice: This patent is subject to a terminal disclaimer.

[21] Appl. No.: 08/232,502

[22] Filed: Apr. 25, 1994

Related U.S. Application Data

[63] Continuation of application No. 07/986,189, Dec. 7, 1992, abandoned.

[51] Int. Cl.[6] .......... A61M 31/00

[52] U.S. Cl. .......... 604/51; 604/82; 604/416; 604/49; 128/DIG. 13; 128/203.13; 128/898

[58] Field of Search .......... 604/51, 52, 82, 604/416, 48, 49; 128/DIG. 13, 203.13, 898

[56] References Cited

U.S. PATENT DOCUMENTS

| | | | |
|---|---|---|---|
| 4,898,578 | 2/1990 | Rubalcaba, Jr. | 128/DIG. 13 |
| 5,102,408 | 4/1992 | Hamacher | 604/416 |
| 5,807,316 | 9/1998 | Teeple, Jr. | 604/51 |

*Primary Examiner*—John G. Weiss
*Assistant Examiner*—Dennis Ruhl
*Attorney, Agent, or Firm*—Titus & McConomy LLP

[57] ABSTRACT

The present invention relates to a method of preparing and administering one or more drug solutions for continuous infusion. Flow rates are standardized by varying the drug concentrations according to a preestablished set of tables. The method of the present invention greatly simplifies clinical application of continuous infusion anesthesia, and allows easy preparation of different volumes which can minimize drug wastage. The standardization of rate taught by the present method eases interpretation and mixing, resulting in easier application of drugs and increased patient safety. An apparatus is desirably used to assist in achieving the objectives of the present invention. The device facilitates accurate and efficient conversion to the nonstandard flow rates required for special applications such as neonatal anesthesia and others. A computerized mix controller coupled with a computer capable of performing the mixing determination with the necessary operator inputs can mix and dispense the final drug solution into a ready-to-use bag. Users of the method and computer may easily convert to the selection nonstandard flow rates required for special situations such as neonatal anesthesia or others, where low flow rates may be required. Premeasured amounts of anesthetic drugs may be dispensed manually or using the computerized mix controller, resulting in increased safety to patients due to the standardized drug amounts would be prepared by the manufacturer.

10 Claims, 4 Drawing Sheets

A MIXED BAG CORPORATION

NAME ______________________________

DATE ____ PT ID # ____________________

WEIGHT ______ lbs kg

DRUG ______________________________

USE IV SED/ANALOG N20 SUPPL PRIMARY ug/kg/min ______________

DURATION ______________ HOUR mls/HOUR ______________ MAX RATE

VOLUME BAG ____________ ml mls TO REMOVE AND REPLACE WITH

DRUG __________ ml mg DRUG IN BAG ________ mg ug

BAG MIXED BY ________________

FIG. 1

METHOD AND APPARATUS FOR PREPARING AND ADMINISTERING INTRAVENOUS ANESTHESIA INFUSIONS

This is a continuation of application Ser. No. 07/986,189 filed on Dec. 7, 1992, abandoned.

FIELD OF THE INVENTION

The present invention relates to a method and apparatus for preparing solutions of drugs for continuous infusion to a patient, and especially to an improved, cost effective and reliable method and apparatus for use by qualified physicians in which the amount of drug required is determined on the basis of a standardized infusion rate.

BACKGROUND OF THE INVENTION

Many classes of intravenous agents can be used in the treatment of medical patients, such as general anesthesia or an inhalational anesthetic supplements; neuromuscular blockers and paralysis drugs; cardioresuscitative drugs for critical care applications; and many others. For example, anesthesiologists often employ one or more drugs for continuous infusion techniques. However, this practice may be cumbersome and difficult because of the large number of variables involved and the difficulty of remembering each important factor involved in administering one or a combination of drugs. Hence, practitioners often choose to administer one or two agents only and memorize the requirements related to those specific agents and-or standardize a drug mix and vary the delivery rate for each patient, all in hopes of reducing the possibility of error.

The most common method present requires physicians to determine the doses they are giving according to the following cumbersome equation:

$$D \times BW \times 0.06 = C \times R$$

The variables for this equation are defined as follows:

D=Dosage Rate=$\mu g \cdot kg^{-1} \cdot min^{-1}$

BW=Body Weight=kg

C=Concentration of infusion=$mg \cdot ml^{-1}$

R=Rate of infusion=$ml \cdot hr^{-1}$ (Constant=60 $min \cdot hr^{-1} \cdot 1$ mg.1000 $\mu g^{-1}$=0.06)

This equation includes five "unknowns" (the "C" comprising two variables: the numerator (weight in mg) and the denominator (volume in ml)), requiring that a series of calculations be performed each time a drug mix is prepared and used. These intricate calculations make application of the infusion techniques laborious, and increase the risk of human error. The pressures of providing critical health care, coupled with the long and late hours worked by care providers, make desirable any method that reduces the potential for error.

Due to varying body weights of patients, the desired drug flow rates will vary. It becomes very difficult during clinical procedures to repeatedly reevaluate the dosage of drug the patient is receiving. One method of dealing with this problem has been to standardize the drug concentrations. However, a significant problem continues to exist with this method: the delivery rate still varies. Computerized delivery systems that automatically adjust the rates to anesthesia requirements have been used, but such systems are extremely expensive, making them economically impracticable for many operating rooms. Further, the administration of anesthesia is an art as well as a science, and that a computerized system cannot entirely replace the need for the administering physician to understand the factors involved in the application of each drug so as to facilitate proper evaluation of the patient's clinical response.

The many classes of intravenous agents that can be used greatly complicate the practitioner's task. Anesthesiologists more often employ one or more drugs for continuous infusion techniques. As such, prior methods are cumbersome if not undesirable because of the large number of calculations required and the difficulty of remembering all of the variables and factors involved. Hence, many practitioners select one or two agents to simplify the otherwise complex formulas that must be used, and memorize the administration requirements related to these one or two specific agents.

A variety of patents and other references disclose methods and apparatuses for the preparation and administration of intravenous anesthetic drugs.

U.S. Pat. No. 4,853,521 discloses a system for verifying and recording drug administration to a patient, including computerized system to run delivery.

U.S. Pat. No. 4,058,120 discloses a vaporizer carousel for anesthesia machine.

U.S. Pat. Nos. 4,246,894 and 4,334,526 disclose a method and system for administering a dissociative unconscious type of anesthesia.

U.S. Pat. No. 5,015,781 discloses an Anesthetic compound and method of preparation.

U.S. Pat. No. 4,917,670 discloses a continuous spinal anesthesia administering apparatus and method.

U.S. Pat. No. 4,873,076 and similar references disclose a method of safely providing anesthesia or conscious sedation.

U.S. Pat. No. 4,825,860 discloses a device for supplying anesthetic dispensing systems.

U.S. Pat. No. 4,053,604 discloses a method for improving anesthesia mixtures and compositions.

Paul F. White, in his article "Clinical Uses Of Intravenous Anesthetic And Analgesic Infusions" *Anesthesia and Analgesia* 1989;68:161–71, describes clinical applications of continuous infusion anesthesia, but does not contemplate the improved methods of the present invention.

Infusion pumps are also well-known, although the expense of these devices can be prohibitive in many clinical settings. See "Infusion Pumps," *Milestones in Anesthesia*, pp.2–3.

See also, Burtles, Richard; "Continuous Infusion Of Drugs: A Simple And Rational System." *Journal of Cardiothoracic and Vascular Anesthesia* 1991;5(4):362–364; Tilden, Samuel and Hopkins, Robert L.; "Calculation Of Infusion Rates Of Vasoactive Substances." *Annals of Emergency Medicine* 1983;12:697–99;

It has therefore become desirable to develop a method and apparatus for preparing drug solutions for continuous infusion that do not suffer from the shortcomings of prior methods and apparatuses.

SUMMARY OF THE INVENTION

Generally, the present invention is a method and apparatus for preparing a drug solution for continuous infusion which is capable of executing the following steps: establishing a standardized dosage rate; establishing a standardized rate of infusion; and determining the required concentration of the drug on the basis of the weight of the patient, the standardized dosage rate and the standardized rate of infusion. Preferably, these steps are repeated for a number of drugs at incremental weights to establish a reference table of required concentrations. The concentrations are preferably determined on a per unit milliliter basis to enable easy determination of the amount of the drug to be added to the infusion bag. Furthermore, the standardized dosage rate is preferably the maximum maintenance infusion rate established for that drug.

Anesthesia as prepared according to the present invention is induced according to standard anesthetic techniques. An appropriate loading dose is administered to induce anesthesia; following induction, the maintenance infusion is started and maintained. Anesthetic requirements vary, according to the operative procedure to be performed, the health and condition of the patient, the length of the procedure, and numerous other factors. (See Table 1.)

use to be recalculating how much drug the patient is receiving all the time. The use of this method due to its standard delivery of the maximum rate (generally 30 ml-hr) makes dosage interpretation much easier for the physician and much safer for the patient. The use of the present method allows the use of simple, less expensive infusion pumps that are already commonly used if not already available in the clinical setting. Hence, there are also significant cost benefits to the application of the method of the present invention in the operating room or virtually any clinical setting.

Other proposed solutions for dealing with difficulties associated with anesthesia administration have included

TABLE 1

RANGE OF PLASMA CONCENTRATIONS AND PHARMACOKINETIC VARIABLES USED TO DETERMINE LOADING DOSES AND INITIAL MAINTENANCE INFUSION RATES*

| DRUG (TRADE NAME) | Cp ($\mu g \cdot ml^{-1}$)** | Vc ($L \cdot kg^{-1}$) | Vdss ($L \cdot kg^{-1}$) | CL ($ml \cdot kg^{-1}\ min^{-1}$) |
|---|---|---|---|---|
| Thiopental (Pentothal ®) | 5–20 | 0.4 | 2.5 | 3 |
| Methohexital (Brevital ®) | 1–4 | 0.3 | 2 | 11 |
| Etomidate (Amidate ®) | 0.1–0.5 | 0.3 | 4 | 17 |
| Propofol (Diprivan ®) | 1–10 | 0.3 | 2 | 30 |
| Morphine Sulfate | 0.02–0.2 | 0.3 | 3 | 14 |
| Meperidine (Demerol ®) | 0.3–2.0 | 0.7 | 4 | 11 |
| Fentanyl (Sublimaze ®) | 0.002–0.035 | 0.6 | 4 | 13 |
| Sufentanil (Sufenta ®) | 0.0002–0.002 | 0.1 | 2.5 | 11 |
| Alfentanil (Alfenta ®) | 0.05–0.5 | 0.15 | 0.7 | 6 |
| Ketamine (Ketalar ®) | 0.5–2.5 | 0.5 | 3 | 18 |
| Midazolam (Versed ®) | 0.05–1.0 | 0.4 | 1.5 | 7 |

*Values derived by averaging data available from the anesthesia and pharmacokinetic literature.
**Factors that determine the clinically effective plasma drug concentration include patient's age, drug history, level of anxiety, type of operation, and supplemental agent.

Under the present invention, a standardized infusion rate of 30 $ml \cdot hr^{-1}$ is used as a standard to deliver a high (or "maximum") infusion dosage. If the continuous infusion drug is intended to be a supplemental anesthetic agent, the infusion rate should be decreased accordingly. FIG. 1 shows that at 30 $ml \cdot hr^{-1}$, all drugs are being delivered at the high rate. FIG. 1 eases the interpretation of low to high rates for ten relevant anesthesia drugs.

The present invention may also use an apparatus for determining and/or preparing a drug solution for continuous infusion, which may include:

1. a means for inputting data;
2. a memory means for storing data, the memory means having stored therein a predetermined dosage rate for the drug and a standardized rate of infusion;
3. a means operable to determine a required concentration of the drug on the basis of the predetermined dosage rate, the standardized rate of infusion and a patient weight supplied via the input means; and
4. a means for displaying the required concentration and/or preparing the final mixed bag of drugs and dilute to be administered.
5. a means for mixing diluent and drug concentrate(s) into a final mixed bag ready for administration.
6. a means for marking the constituents on the outside of each final mixed bag.

The method and apparatus of the present invention offers a number of benefits over other methods of mixing and administering anesthesia. Prior methods require physicians to calculate the doses they are giving according to a cumbersome formula. Because patients has different body weights, drug solution flow rates will necessarily vary accordingly. It thus becomes very difficult during clinical standardizing as to drug concentration(s); however, problems with this method remain in that the delivery still must vary. The use of computerized infusion delivery systems that automatically adjust the rates to anesthesia requirements can be prohibitively expensive and therefore not a practical solution in many settings.

Anesthesia and other drugs to be administered according to the present invention may be prepared from vials with premeasured doses, for patients within a specified weight range to eliminate mixing steps that would otherwise be necessary, thereby reducing the risk of human error. The present method is also useful for administering a broad range of drugs, including muscle relaxants, sedatives and analgesics. This infusion method can again be used both in the operating room and in the intensive care unit pharmacy, outpatient medical and dental facilities, or any number of clinical situations.

The present method is applicable to a variety of types of drugs, including, but not limited to, anesthetics, muscle relaxants, sedatives, analgesics and cardioresuscitative drugs. The method of the present invention offers a number of benefits over prior methods of mixing and administering such drugs. The present method, because of standardization of the dosage rate, makes interpretation much easier for the physician and much safer for the patient. The present method also allows the use of simpler and much less expensive infusion pumps that are already easily available in the clinical setting. The method is equally useful in the operating room, intensive care unit, or elsewhere in the hospital environment.

Furthermore, if drugs are supplied in vials with premeasured doses, calculation steps are completely eliminated, thus further increasing the safety of the method. Premeasured vials of drug concentrate may be bar coded or otherwise encoded with a machine readable data set (drug type, freshness date, concentration, volume, etc.) so as to insure that the proper drug mix is achieved, reducing if not eliminating the possibility for human error. The present method also allows greater flexibility in selection of an agent to use for a continuous infusion anesthetic or analgesic. Physicians relieved of the difficulties of prior methods of preparing anesthetics will be encouraged to widen the number of and types of drugs they use for continuous infusions. Physicians are thus able to use the best combinations of drugs with reduced risk of inappropriate dosing.

BRIEF DESCRIPTION OF THE DRAWINGS

The invention will become more readily apparent from the following description of preferred embodiments thereof shown, by way of example only, in the accompanying drawings wherein:

FIG. 1 is the first embodiment of the present invention;

DETAILED DESCRIPTION OF THE INVENTION

Method of the Present Invention

Figure 2:
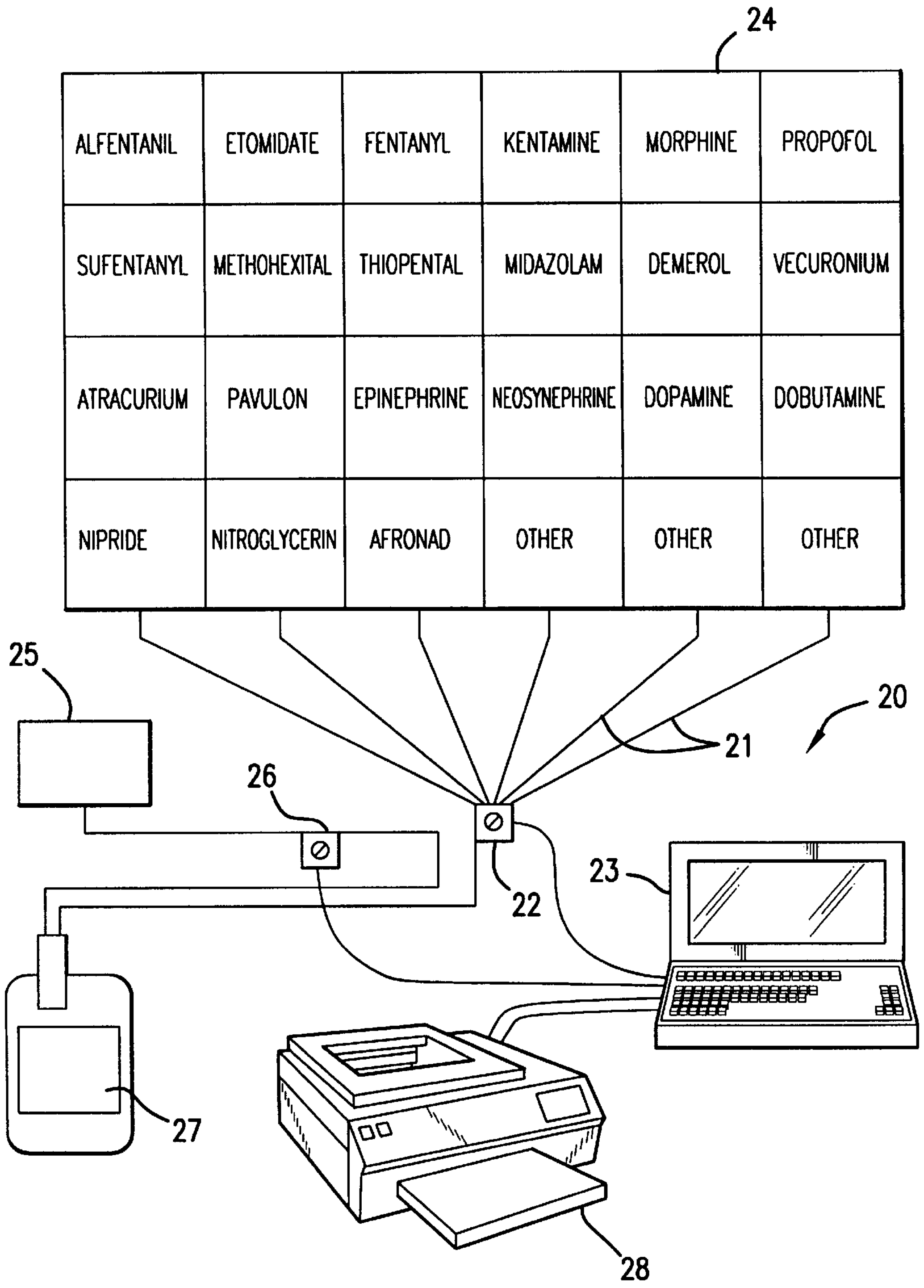
FIG. 2 is the second embodiment of the present invention.

Use of a table that has predetermined values can eliminate many of the required steps in preparing the anesthetics to be administered, and tables that follow. Each variable is also defined and explained.

Dosage (D)

White proposes the use of clinically determined high and low values for continuous infusion techniques. The value for Maintenance Infusion Rates (MIR) in White is determined by multiplying the plasma concentration (Cp) by the clearance (CL). The Cp column gives the high and low values of the range for each agent.

For the determination in Table 2, the high value of Cp will always be selected so that the infusion will contain the concentration and volume required to supply the highest expected need [e.g., for Thiopental {20 $\mu$g·ml$^{-1}$(Cp Max).3 ml kg$^{-1}$ min$^{-1}$ (CL)}=(60 mg·kg-1·min−1)]. Hence for the Table 2, D will equal MIR-High level for each agent.

Body Weight (B.W.)

Body weight is a fixed value for each individual patient. In the table used here, a column of values will be created for each 10 kg increase in weight.

Constant

The constant 0.06 corrects for unit of measurement differences between the dosage and the infusion rate (ml-hr).

Rate Of Infusion (R)

Nominally, rate of infusion can be any selected value. However, to simplify and standardize the infusion rates for all the intravenous agents, the rate will be set at 30 ml·hr$^{-1}$·(1) This standardization of the high-MIR dosage with a rate of delivery will make the application of all intravenous infusion anesthetics consistent.

Concentration Of Infusion (C)

The concentration of the infusion mixture is given in mg-ml. This term will be referred to hence forth as the Concentration Multiplier (C*). The values in Table 2 will be equal to C*.

Table 2 Determination
For purposes of demonstration, as consistent with the foregoing text, the following assumptions have been made:

| | |
|---|---|
| D = | MIR High |
| BW = | Fixed Weight Per Column |
| R = | 30 ml · hr$^{-1}$ |
| C* = | $\frac{\text{Numerator Unknown}}{\text{Denominator} = 1\text{ ml}}$ = Concentration Multiplier |

Taking the original equation and solving for C* (for each drug at each kg wt), Table 2 is generated. Selection of, 1) the desired intravenous agent by row, and 2) the kg weight of the patient by column, allows the practitioner to choose C*. C* equals the number of mg per ml of dilute in the infusion bag. This mixture will deliver the MIR high if the infusion pump is set to deliver 30 ml per hour.

The only exception to the Table 2 method is the drug Propofol, which cannot be mixed to a concentration desirable for this methodology. However, if mls·$^{-1}$ is increased to 120 ml·hr$^{-1}$, then a technique consistent with the present method can be employed.

TABLE 2

| | C* AT DIFFERENT Kg WEIGHTS (weight in kgs) | | | | | | | | |
|---|---|---|---|---|---|---|---|---|---|
| DRUG SELECTED | 120 | 110 | 100 | 90 | 80 | 70 | 60 | 50 | 40 |
| Thiopental | 14.4 | 13.2 | 12 | 10.8 | 9.6 | 8.4 | 7.2 | 6 | 4.8 |
| Methohexital | 10.56 | 9.68 | 8.8 | 7.92 | 7.04 | 6.16 | 5.28 | 4.4 | 3.52 |
| Etomidate | 2.04 | 1.87 | 1.7 | 1.53 | 1.36 | 1.19 | 1.02 | 0.85 | 0.68 |
| Propofol* | — | — | — | — | — | — | — | — | — |
| Morphine | 0.672 | 0.616 | 0.56 | 0.504 | 0.448 | 0.392 | 0.336 | 0.28 | 0.224 |
| Meperidine | 5.28 | 4.84 | 4.4 | 3.96 | 3.52 | 3.08 | 2.64 | 2.2 | 1.76 |
| Fentanyl** | 0.0108 | 0.0099 | 0.009 | 0.0081 | 0.0072 | 0.0063 | 0.0054 | 0.0045 | 0.0036 |
| Sufentanil | 0.00528 | 0.00484 | 0.0044 | 0.00396 | 0.00352 | 0.00308 | 0.00264 | 0.0022 | 0.00176 |
| Alfentanil | 0.72 | 0.66 | 0.6 | 0.54 | 0.48 | 0.42 | 0.36 | 0.3 | 0.24 |
| Ketamine | 10.8 | 9.9 | 9 | 8.1 | 7.2 | 6.3 | 5.4 | 4.5 | 3.6 |
| Midazolam | 1.68 | 1.54 | 1.4 | 1.26 | 1.12 | 0.98 | 0.84 | 0.7 | 0.56 |

*Propofol — Unable to mix 30 IMED rate use package inset.
**Figures are ten times less than absolute doses, useful for supplemental anesthesia only.

Procedure 1: Mixing The Infusion Bag

| | | |
|---|---|---|
| A) | Body weight of patient = | kg = [ ] |
| B) | Select intravenous agent | Agent = [ ] |
| C) | Choose appropriate column and row of Table 2 to select Concentration Multiplier (C*). | C* = [ ] |
| D) | Volume of Infusion Bag Required Expected duration [ ] hrs × 30 ml-hr needed = ml[ ] of case | |
| E) | Total mg of Agent Required | mg = [ ] |
| F) | Volume of Drug | |
| | $[\ ]\text{mg}\cdot\dfrac{1}{[\ ]\ \text{mg}-\text{ml undulated drug}}=$ | volume of drug ml* = [ ] |
| G) | Remove ml* amount from infusion bag | |
| H) | Add ml* amount of intravenous agent to infusion bag. | |
| I) | Label bag | |
| J) | Hook up bag to infusion device that delivers ml-hr. | |

(Note: If D. volume of infusion bag is set = 100 ml, you need only shift decimal points of values in Table 2 until Step F)

Procedure 2: Loading Dose Determination

| | | | | |
|---|---|---|---|---|
| A) | Select BW – [ ] kg | | | |
| B) | Choose intravenous agent loading dose from Table 3. Table 3 gives high and low dose ranges for the agent. The dose range is for use of the drug as a primary anesthetic. If the drug is to be a supplemental agent, lower doses should be used. | | | |
| | Loading Dose | | | |
| | High Dose | [ ] · [ ] kg = [ | ] mg | |
| | Average Dose | [ ] · [ ] kg = [ | ] mg | |
| | Low Dose | [ ] · [ ] kg = [ | ] mg | |

TABLE 3

| | LOADING DOSE* | | |
|---|---|---|---|
| DRUG SELECTED | HIGH $MG \cdot KG^{-1}$ | AVERAGE $MG \cdot KG^{-1}$ | LOW $MG \cdot KG^{-1}$ |
| Thiopental | 8 | 5 | 2 |
| Methohexital | 1.2 | .75 | 0.3 |
| Etomidate | 0.15 | .09 | 0.03 |
| Propofol | N-A | N-A | N-A |
| Morphine | 0.06 | .033 | 0.006 |
| Meperidine | 1.4 | .805 | 0.21 |
| Fentanyl | 0.021 | .0111 | 0.0012 |
| Sufentanil | 0.0002 | .00011 | 0.00002 |
| Alfentanil | 0.075 | .0412 | 0.0075 |
| Ketamine | 1.25 | .75 | 0.25 |
| Midazolam | 0.4 | .21 | 0.02 |

*Table 3 loading dose values are based on the MIR doses recommended in White. For each agent, a Cp plasma concentration high and low range was multiplied by Vc (central volume) to arrive at the loading dose $mg \cdot kg^{-1}$.

The actual loading dose will be determined by the clinician based on the clinical status of the individual patient.

Anesthetic Induction And Maintenance

Anesthesia will be induced according to standard anesthetic technique. The appropriate loading dose will be given to induce anesthesia. Following induction, the maintenance infusion will be started. The infusion rate of 30 $ml \cdot hr^{-1}$ is selected to deliver the high MIR recommended in White's article. If the continuous infusion drug is intended to be a supplemental anesthetic agent, the infusion rate should be decreased accordingly.

Figure 4:
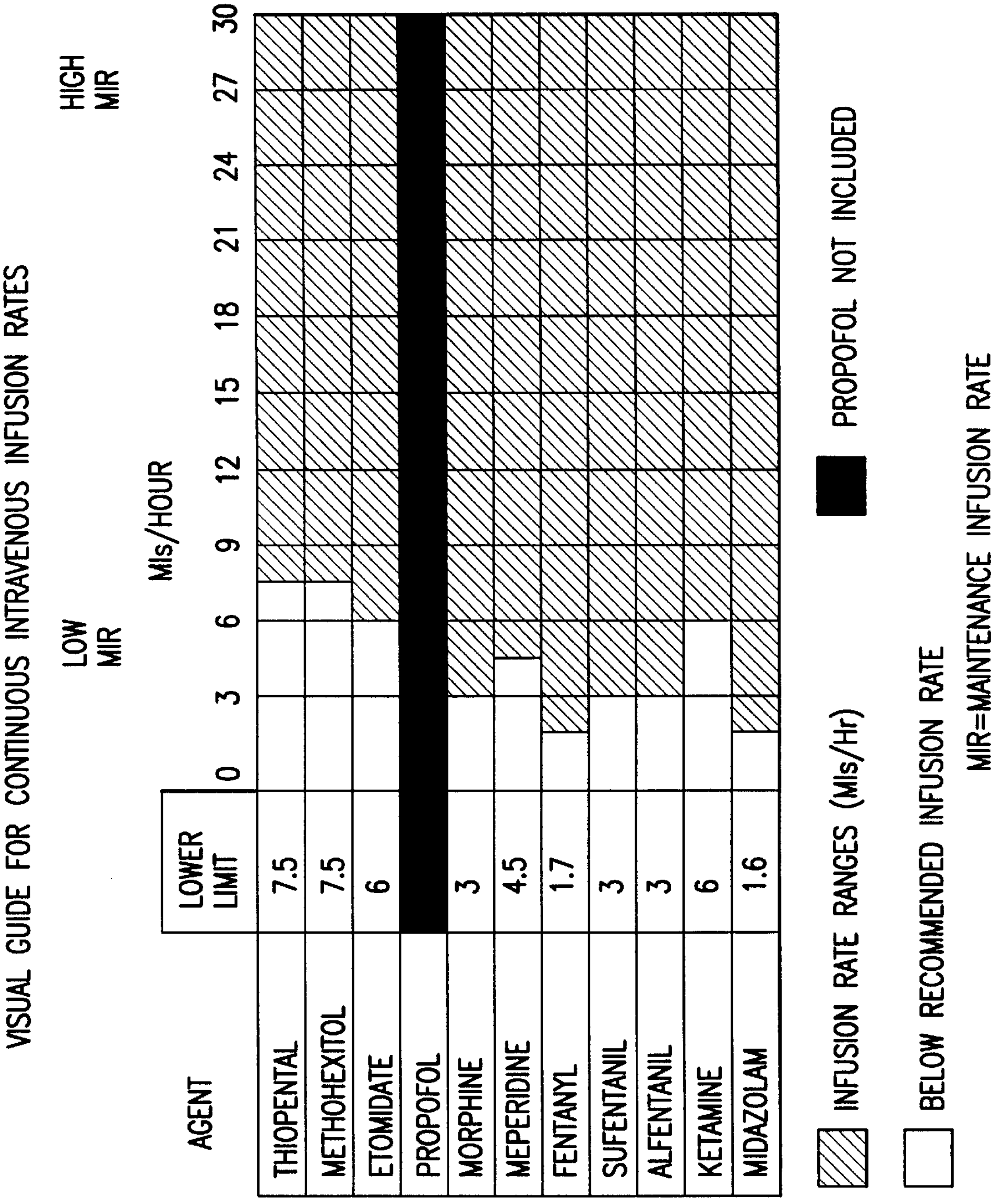
FIG. 4 is a chart showing known drug dosage levels.

The desired individual anesthetic administration requirements may vary greatly. FIG. 4 shows the high-low delivery rates which reflect the values given in White (Table 4). Keeping the flow rates within the checkered area will deliver the recommended dosage levels. FIG. 4 allows the practitioner to visually evaluate where the infusion falls in the rank of the selected high-low maintenance infusion rates.

During anesthetic administration, the MIR should be serially lowered to maintain the lowest tolerable infusion rate. This will allow for quicker patient wake up at the end of the procedure.

Example Administration of Anesthesia

An example using Tables 2 and 3 will now be presented. A 60 kg female is to undergo an abdominal hysterectomy. A Thiopental-Succinylcholine induction is planned. A supplemental Fentanyl infusion combined with Isoflurane at 1–2 MAC will be used for maintenance anesthesia. The duration of the case is expected to be three hours. To determine loading dose of the selected drug (Fentanyl), Table 3 is used.

The loading dose determination is as follows:

Avg. Loading Dose: [0.0111]×[60] kg 0.666 mg 666 mg

High Loading Dose: 0.021×60 1.260 mg=1260 mg

Low Loading Dose: 0.0012×60 0.072 mg 72 mg

Procedure 1, (mixing the bag for infusion drip) is then performed:

A) BW=60 kg

B) Agent=Fentanyl

C) C* 0.0054 mg-ml (from Table 2)

D) Hrs[3]·30 ml-hr=90 ml→will mix 100 ml

E) Total mg required [100 mls.]·C* [0.0054] mg-ml=0.54 mg

F) Fentanyl [0.54 mg]·[0.050] mg-$ml^1$=[10.8] ml* drug

G) Remove 10.8 ml of fluid from infusion bag.

H) Add 10.8 ml of 0.05 mg-ml Fentanyl to bag.

I) Label bag.

J) Hook up infusion device that delivers ml-hr. Set device to 10–15 ml-hr to start.

For the induction phase of actual anesthetic delivery, the selected loading dose will be given as an immediate intravenous premedication or as part of the anesthetic induction. Following the induction phase continuous infusion of Fentanyl will be started at 15 ml-hr. (See FIG. 4.) The infusion rate will be titrated to effect using the guidelines suggested in FIG. 4 of White.

Once level of anesthesia is obtained, the rate of the continuous infusion of Fentanyl is serially lowered, so as to maintain effective analgesia while minimizing drug accumulation. The infusion should be stopped, as tolerated by patient, 20–30 minutes prior to the end of surgery to allow for quick wake-up. For a more detailed description of the method of continuous infusion anesthesia, the reader is referred to White's article.

Computer Program For Determining Drug Mixes

FIG. 1 shows a sample computer screen output and-or final mixed bag label listing the mixing determination. The computer is programmed according to the method outlined above, so that upon input by the user of the requisite data under the method, the program executes the steps of dosage determination for the operator. The results of the dosage determination (including the information shown in FIG. 1) may preferably be printed out an adhesive-backed label for manual or automatic attachment to the final mixed bag.

Users of the computer program may easily tailor the diluent and drug concentration mixtures to the selection any standard or nonstandard flow rate, according to the most desirable application of drugs; such custom mixes result in important patient safety benefits in many special situations such as neonatal anesthesia or others, where specialized flow rates may be required.

Computerized Mix Controller For Preparing Drug Mixes

FIG. 2 shows the layout for a computerized mix controller 20 for preparing drug mixes. The computerized mix controller is capable of performing the mixing determination, and then mixing drugs from drug matrix 24 through supply lines 21 (controlled by multiport drug concentration valve 22) and diluent from vessel 25 (controlled by diluent valve 26) so as to mix the infusion bag 27 for the practitioner. Computer 23 is preprogrammed according to the method of the present invention so that upon input by the user of the requisite variables, and execution of the appropriate command, the device completes the steps of dosage determination, infusion bag mixing and labeling (as output by automatic label maker 28) for the operator. Computer 23 may also be equipped with an alarm capable of alerting the operator of system malfunction, insufficient quantities of diluent or drug concentrate, program error and/or improper data entry. The results of the dosage determination (including all information displayed on the screen shown in FIG. 1) are printed out by label maker 28 for attachment to the final mixed bag.

The computerized mix controller is equipped with a flow meter-valve system so that upon input of the appropriate command, the necessary diluent dispensed into the supply bag. The necessary drug concentrates are thereafter dispensed from individual vessels into the supply bag, again using a valve, flow meter or carousel and valve setup. After the computerized mix controller dispenses the final amounts of drug and diluent into the supply bag, this bag may be manually or automatically sealed, and an adhesive-backed label with the final mix information may be manually or automatically affixed to the bag.

Rather than requiring as per prior art system (also utilizing a different method) that a complex electronic, pressure or other infusion pump means be used for each patient for the duration of an operation, the apparatus of the present invention permits a single device to prepare infusion bags at a rapid rate for an entire medical complex or even multiple facilities. A hand held, lap-top or desktop computer may be used by the practitioner at each patient infusion site, or again at a centralized location.

The drug concentrates may most desirably be stored in a temperature-controlled environment prior to use; the infusion bag may after mixing likewise be maintained in this controlled environment. The computer program is also desirably equipped with a shelf-life monitoring function; when the shelf-life of a drug expires, the operator may be notified, or a fresh drug concentrate vial may automatically be moved into place, and the expired vial automatically disposed of. A bar code reader system may be used to monitor expiration date, and to monitor that the correct drug concentrate has been loaded into the automatic mix controller.

Figure 3:
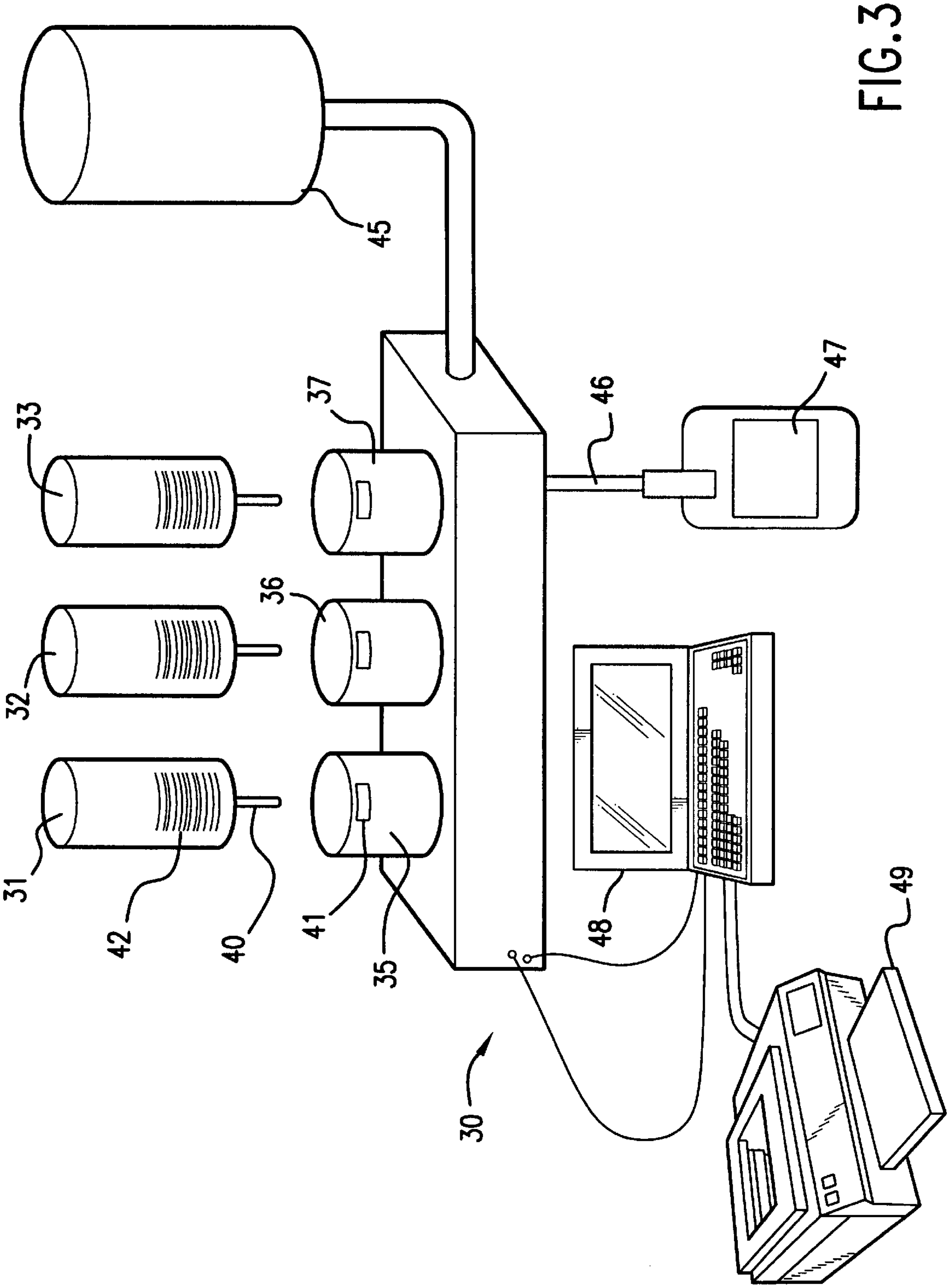
FIG. 3 is the third embodiment of the present invention.

FIG. 3 shows a device 30 for preparing drug mixes. Drug concentrate vials 31, 32 and 33 are inserted into receptacles 35, 36 and 37. Computer terminal 38 is preprogrammed according to the method of the present invention so that upon input by the user of the requisite variables, and execution of the appropriate command, the device completes the steps of dosage determination and infusion bag mixing for the operator. The results of the dosage determination may again be printed out for attachment to the final mixed bag.

A fluid connector 40 on each drug concentrate vial permits the drug from each vial to be measure by a valve or flow meter and thereafter pumped or drained through supply line 46 into mixed bag 47. A bar code reader 41 monitors the drug type and expiration date of the drug in each drug concentrate vial, as indicated by bar code 42 on each vial. If an incorrect drug concentrate has been loaded into the automatic mix controller 48, or the drug is no longer fresh, an alarm may sound, and-or the device may automatically disable to prevent an incorrect or stale drug from being dispensed. Diluent supply 45 provides the required diluent for the final mixed bag 47. Label maker 49 may manually or automatically apply an adhesive-backed data label to the final mixed bag. The computer is preprogrammed according to the method of the present invention so that upon input by the user of the requisite variables, and execution of the appropriate command, the device completes the steps of dosage determination and infusion bag mixing for the operator. The results of the dosage determination (including all information displayed on the screen shown in FIG. 1) may again be printed out for attachment to the final mixed bag.

SUMMARY

The method and apparatus of the present invention standardizes and simplifies use of continuous intravenous infusion anesthesia and analgesia. Institutions that would rigorously apply the suggested mixes would standardize all infusion rates for all the listed drugs.

By simplifying the dosage determinations, and by utilizing the computer and-or computerized mix controller, practitioners are encouraged to use all available anesthetic agents. The present method is effective for primary or supplemental anesthetic agents, analgesic agents and sedative agents. Finally, the procedure allows for ready mixing of any required volume of infusion drug. This allows for mixture of an expected volume of drug for a specific duration case. This will result in less wastage of drug.

Descriptions of the clinical applications of continuous infusion anesthesia are set forth in White and are not repeated herein. FIG. 4 (known) allows the practitioner to have a ready visual reference of the range of continuous MIR infusion rates. For primary agent applications, use of the higher range is appropriate (20–30 ml/hr). For supplemental or sedative agent applications, use of rates of 10–20 ml/hr would be more appropriate. For mild analgesic effects of the drug, rates of <10 ml-hr would apply. One must always remember to adjust the dose according to clinical needs.

Most practitioners are more comfortable evaluating drug usage under the "total dose" concept. Using this concept, the C* (see Table 2) selected (mg-ml) times (total ml's given) will equal total dose. This can perhaps best be visualized by the similar vaporizer/percent delivery concept.

A desirable method and important advancement in the pharmaceutical delivery industry included in the present invention is the use of premeasured (and standardized) vials of anesthetic drugs, with bar coded data labels. These vials should desirably coincide with the parameters set forth in Table 1. This allows standardized and easier mixing of the drugs for the practitioner. This would again increase safety due to the fact that the drug amounts would be determined by the manufacturer.

When an apparatus (computer, or the like) is used to complete the determination of the required mixes of the various drugs to be used in the method of the present invention, that apparatus may be coupled with a printer to output a label to be attached to the anesthesia bag. It would also be possible for an automated mixing system to prepare the drug solutions using the premixed vials or similar method of calibrating the required volumes/weights of drugs and dilute to be used in a drug delivery bag.

The method of the present invention can be tailored according to the described formulations to meet specific desired performance characteristics for a wide variety of intravenous drug applications. Although the method for administering anesthesia offered by the present invention have been described in detail in the foregoing for purposes of illustration, it is to be understood that such details are solely for that purpose and that variations may be made therein by those skilled in the art without departing from the spirit and scope of the invention as described in the following claims.

What is claimed is:

1. A method for preparing a solution with at least one drug for an infusion bag for providing continuous infusion into a patient, comprising the following steps:

a. determining a dosage rate for a maximum dosage at a standardized maximum rate of infusion for said drug;

b. establishing a standardized titration rate range of infusion;

c. determining a required concentration of at least one drug based on a patient's weight, said dosage rate, amount of said solution, and standardized maximum rate of infusion;

d. mixing said drug into a bag of diluent to the concentration determined in Step C.

2. The method of claim 1 wherein said dosage rate is determined as a maximum maintenance infusion rate x and a minimum rate x13 for said drug.

3. The method of claim 1 wherein the drug is for intravenous infusion of anesthetics.

4. The method of claim 1 wherein steps a, b and c are repeated for a number of commonly used drugs at incremental patient weights and a table is created giving the required concentration for each drug at each incremental patient weight.

5. The method of claim 4, wherein step d comprises mixing said drugs and a diluent according to the required concentrations of step c.

6. The method of claim 1 wherein a concentration for a number of drugs is established at incremental patient weights to create a reference table giving said concentration for each drug at each incremental patient weight.

7. The method of claim 6 wherein vials of each drug are prepared at an established concentration for each incremental patient weight.

8. A method as claimed in claim 1 wherein said standard infusion rate is 30 ml/hr.

9. A method as claimed in claim 1 wherein said standard infusion rate is 120 ml/hr where said drug is propofol.

10. The method of claim 1 wherein a concentration for a number of drugs is established at incremental patient weights for use in a software program used to control mixing of each drug for infusion at each incremental patient weight.

* * * * *